United States Patent [19]

Glover

[11] Patent Number: 5,201,758
[45] Date of Patent: Apr. 13, 1993

[54] DISPOSABLE TOURNIQUET CUFF

[75] Inventor: Dennis Glover, Jackson, Mich.

[73] Assignee: Boehringer Mannheim Corporation, Indianapolis, Ind.

[21] Appl. No.: 817,664

[22] Filed: Jan. 7, 1992

[51] Int. Cl.$^5$ ............................................. A61B 17/00
[52] U.S. Cl. ..................................... 606/202; 606/203; 128/686
[58] Field of Search .......................... 606/201–204; 128/677, 686

[56] References Cited

U.S. PATENT DOCUMENTS

| | | |
|---|---|---|
| 800,467 | 9/1905 | Myers . |
| 814,795 | 3/1906 | Myers . |
| 2,511,269 | 6/1950 | Jones . |
| 3,120,846 | 2/1964 | Fletcher . |
| 3,467,077 | 9/1969 | Cohen . |
| 3,504,675 | 4/1970 | Bishop, Jr. . |
| 3,633,567 | 1/1972 | Sarnoff . |
| 3,654,931 | 4/1972 | Hazlewood . |
| 3,669,096 | 6/1972 | Hurwitz . |
| 3,670,735 | 6/1972 | Hazlewood . |
| 3,713,446 | 1/1973 | Sernoff . |
| 3,756,239 | 9/1973 | Smythe . |
| 3,906,937 | 9/1975 | Aronson . |
| 3,930,506 | 1/1976 | Overend . |
| 3,968,788 | 7/1976 | Hopkins . |
| 3,977,393 | 8/1976 | Kovacic . |
| 4,106,499 | 8/1978 | Ueda . |
| 4,321,929 | 3/1982 | Lemelson et al. . |
| 4,354,503 | 10/1982 | Golden . |
| 4,635,635 | 1/1987 | Robinette-Lehman . |
| 4,979,953 | 12/1990 | Spence . |

FOREIGN PATENT DOCUMENTS 3333311  4/1985  Fed. Rep. of Germany ...... 606/202

*Primary Examiner*—C. Fred Rosenbaum
*Assistant Examiner*—William Lewis
*Attorney, Agent, or Firm*—Barnes & Thornburg

[57] ABSTRACT

A tourniquet cuff for reducing blood flow in a patient's limb includes a backing plate having an inner and outer side. A flexible covering having an inner and outer side is also provided. The flexible covering is formed to be substantially more pliable than the backing plate. The backing plate and the flexible covering are attached to each other to define an inflation cavity between the inner side of the backing plate and the inner side of the flexible covering. An inflatable bladder is positioned in the inflation cavity and the tourniquet is secured about a patient's limb with the outer side of the flexible covering in contact with the patient's limb.

21 Claims, 2 Drawing Sheets

DISPOSABLE TOURNIQUET CUFF

BACKGROUND AND SUMMARY OF THE INVENTION

The present invention relates to a disposable tourniquet cuff that can be wrapped around a patient's limb and inflated to reduce blood flow in the limb.

Inflatable tourniquet cuffs are widely used by the medical industry. Typically, a tourniquet cuff is positioned around a limb of a patient, secured in place, and manually or automatically inflated. Inflation of the tourniquet cuff results in the application of pressure to the limb of the patient, substantially reducing blood flow in the portions of the limb distal relative to the inflated tourniquet cuff. After use, the tourniquet cuff is discarded as medical waste.

For example, U.S. Pat. No. 4,635,635 to Robinette-Lehman, issued Jan. 13, 1987, describes an inflatable tourniquet cuff having an inflatable member. The inflatable member includes a flexible backing formed from two pieces. A stiffener is positioned between the two pieces. The two pieces are joined and sealed to form an envelope that holds the stiffener. Two sheets are joined to form a bladder, and the bladder, along with a bladder protective layer, is joined to the envelope.

The inflatable member has a substantially arcuate shape, and is configured to form a shape that is substantially similar to the frustum of a cone when wrapped about a body part. A set of tourniquet cuffs, with sizes selected so that the arcs of the cuff nest within each other is also disclosed. In certain embodiments, the inside radius of one cuff in a set is selected to match the outside radius of the next smaller size cuff.

U.S. Pat. No. 4,979,953 to Spence, issued Dec. 25, 1990, also discloses a disposable, inflatable tourniquet cuff. The disclosed tourniquet cuff includes a pair of flexible opposed and correspondingly sized bladder wall members. Each bladder wall member is formed from a polymer impregnated fabric that can be bonded to each other. A pair of fabric cover members are placed on opposite sides of the bladder wall members, and at least one outermost peripheral stitched border strip joins the cover members to the bladder wall members. A stiffener plate is disposed between one of the bladder walls and one of the cover members. Straps, ties, or other means are used to secure the cuff around a body part. Inflatable tourniquets are also shown in U.S. Pat. Nos. 3,120,846, 3,504,675, 3,654,931, and 3,713,446, but such patents do not show or suggest the present invention.

The present invention provides a tourniquet cuff for reducing blood flow in a patient's limb. The tourniquet includes a backing plate having an inner and outer side. A flexible covering having an inner and outer side is also provided. The flexible covering is formed to be substantially more pliable than the backing plate. The backing plate and the flexible covering are attached to each other to define an inflation cavity between the inner side of the backing plate and the inner side of the flexible covering. An inflatable bladder is positioned in the inflation cavity and the tourniquet is secured about a patient's limb with the outer side of the flexible covering in contact with the patient's limb.

In preferred embodiments, a border strip is positioned for stitching attachment of the backing plate and the flexible covering. The flexible covering is attached to the backing plate by stitching extending through the flexible border strip, the backing plate, and the flexible covering.

In other preferred embodiments, the inflatable bladder further comprises first and second air impermeable layers attached together by an air impermeable seal at their peripheries to provide a bladder chamber defined between the first and second air impermeable layers. To permit inflation of the bladder chamber, an inlet conduit is situated to extend through a hole defined in the backing plate and join in fluid communication with the bladder chamber. A coupling piece configured for attachment to a pressurized air source is attached to the conduit.

In another preferred embodiment, a tourniquet cuff according to the present invention includes a backing plate having an inner and outer side. A strip supporting a plurality of fabric hooks is attached to the outer side of the backing plate, and a fabric strap is attached at one end to the outer side of the backing plate. The fabric strap supports a plurality of fabric loops for engagement with the fabric hooks. A flexible covering having an inner and outer side, formed to be substantially more pliable than the backing plate, is provided. The backing plate and the flexible covering are attached to each other to define an inflation cavity between the inner side of the backing plate and the inner side of the flexible covering. The outer side of the flexible covering is formed to present an engagable surface for engagement with the fabric hooks to augment securement of the tourniquet about a patient's limb, and an inflatable bladder is positioned in the inflation cavity. Inflation of the bladder reduces blood flow in a patient's limb when the tourniquet cuff is wrapped around a patient's limb, the fabric strap is securely attached to the strip, and the strip engages the engagable surface of the flexible covering.

In yet another preferred embodiment, a tourniquet cuff for reducing blood flow in a patient's limb includes a backing plate having an inner and outer side. A flexible covering having an inner and outer side is attached to the backing plate, together defining an inflation cavity between the inner side of the backing plate and the inner side of the flexible covering. The flexible covering is formed to be substantially more pliable than the backing plate, and preferably is formed from a polymeric foam to present a padded surface that helps distribute circumferential pressure to a patient's limb, enhancing patient comfort.

In operation, an inflatable bladder is positioned in the inflation cavity, and the tourniquet cuff is wrappably attached to itself by an engagement mechanism such as fabric hooks and loops, ties, snaps, or other conventional fasteners. Telescoping lateral movement of the wrapped tourniquet cuff is prevented during inflation by a mechanism that can include fabric hooks and loops, or other conventional fasteners. Preferably, a substantial portion of the outer side of the padded foam flexible covering presents an engaging surface to augment securement of the tourniquet about a patient's limb and minimize telescoping lateral movement of the tourniquet.

Additional features and advantages of the invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
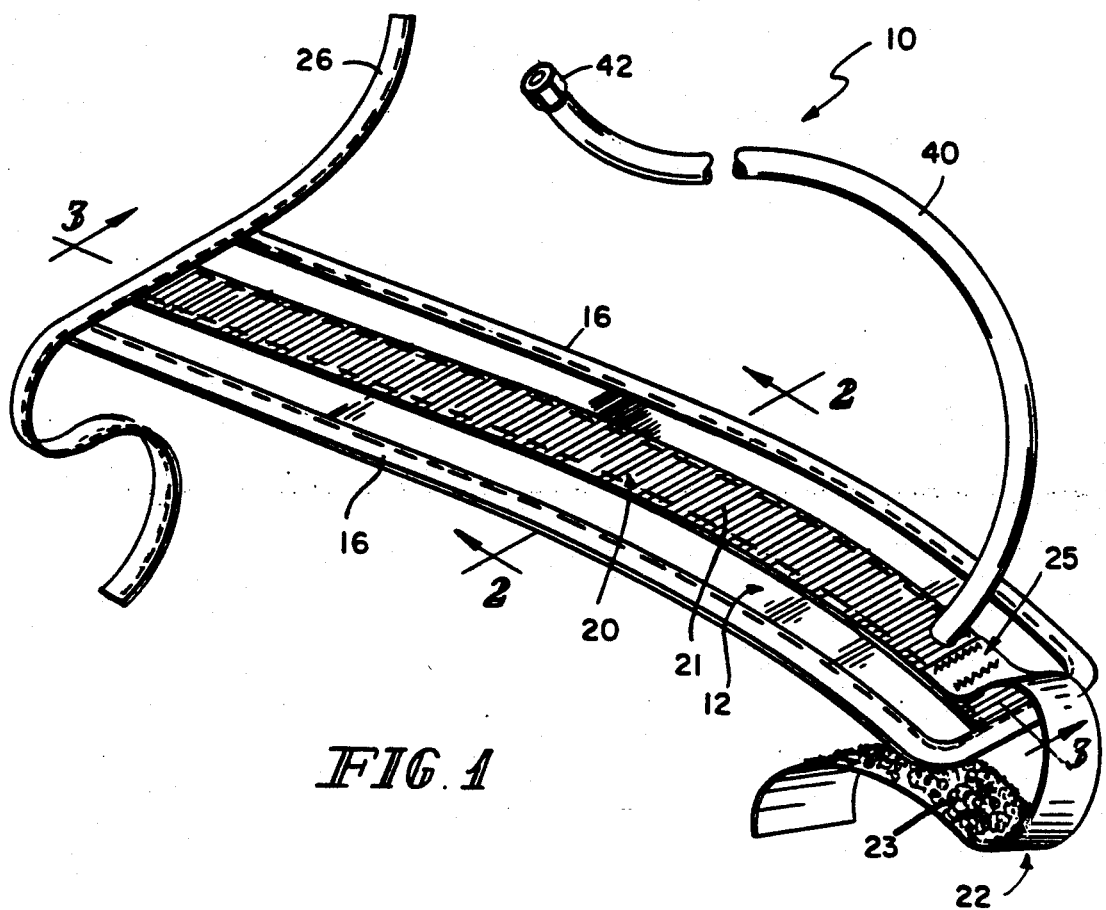
FIG. 1 is a perspective view of an uninflated tourniquet cuff according to the present invention, showing a backing plate having attached fabric hooks and a fabric strap provided with fabric loops to engage the fabric hooks and hold the tourniquet cuff around a patient's limb.
Figure 2:
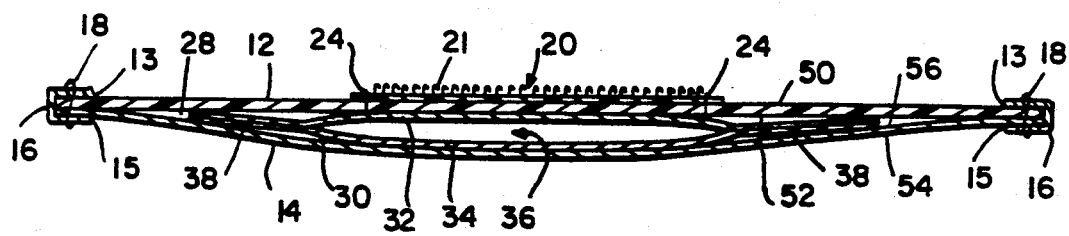
FIG. 2 is a transverse cross sectional view taken along line 2—2 of the tourniquet cuff illustrated in FIG. 1, showing an inflatable bladder disposed between a backing plate and a flexible covering.
Figure 3:
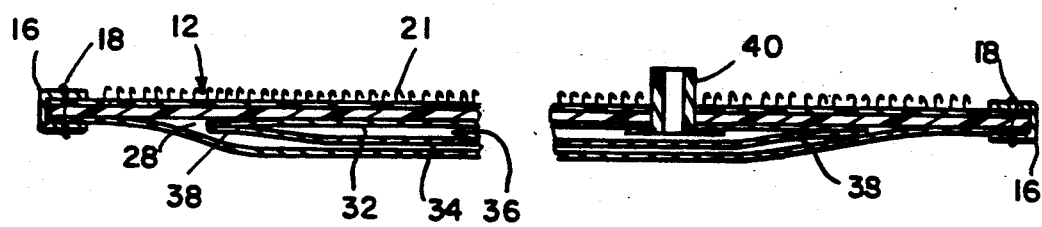
FIG. 3 is a longitudinal cross sectional view taken along line 3—3 of the tourniquet cuff illustrated in FIG. 1, showing an inlet conduit in fluid communication with the inflatable bladder.

As illustrated in FIGS. 1-3, a disposable tourniquet cuff 10 includes a backing plate 12 having in outer side 50 and an inner side 52. A similarly dimensioned flexible covering 14 having and outer side 54 and an inner side 56 is also provided. The backing plate 12 is securely attached by stitching 18 to a flexible covering 14. The stitching 18 extends through a peripherally positioned border strip 16 that is wrapped around an edge 13 of the backing plate and an edge 15 of the flexible covering 14. The stitching is typically nylon thread, mechanically sewn to permanently attach the backing plate 12 and flexible covering 14.

Both the backing plate 12 and the flexible covering 14 are generally rectangular in shape, and the dimensions of backing plate 12 and flexible covering 14 are matched, with the respective length and width being substantially equivalent. The backing plate 12 is constructed from semirigid plastic material that is sufficiently flexible to allow wrapping the backing plate 12 around a patient's limb. Typically, polyethylene, or reinforced polyethylene composites are used because of their low cost, ease of molding a desired shape, and ready availability. However, other types of plastics, reinforced or plastic impregnated fabrics, or other conventional materials can be used to form the backing plate 12. The flexible covering 14 is constructed from durable nylon cloth, although of course other conventional fabrics, or even flexible plastic sheets can alternatively be used.

Since the backing plate 12 and flexible covering 14 are configured to be wrapped around a patient's limb, their respective lengths are usually selected to range from about 20 centimeters to about 60 centimeters, depending upon the specific application. For tourniquet cuffs designed to be wrapped about an adult patient's leg, the lengths are typically selected to range from about 60 centimeters to about 112 centimeters. For tourniquet cuffs designed to be wrapped about an adult patient's arm, the lengths are typically selected to range from about 40 centimeters to about 60 centimeters. The length of tourniquet cuffs designed for use with juveniles will of course be somewhat smaller. It is contemplated to provide a set of tourniquet cuffs having varying lengths to accommodate differing limb size.

The width of the backing plate 12 (and corresponding flexible covering 14) must be sufficient to allow comfortable inward, radially directed application of pressure to a patient's limb. Accordingly, the width is generally selected to range from about 6 centimeters to about 16 centimeters. Typically, a width of 10 centimeters is selected. In those embodiments of the invention in which a set containing varying length sized tourniquet cuffs is used, the width of each tourniquet cuff can be fixed. Alternatively, varying width cuffs for different applications is contemplated. In the latter case, the width can vary as a function of the length of the cuff, for example, being wider with increasing tourniquet cuff length.

The tourniquet cuff 10 is wrapped around and securely attached to itself using a strip 20 permanently mounted on the outer side 50 of the backing plate 12. The strip 20 is provided with a plurality of fabric hooks 21. In addition, a fabric strap 22 is attached at its attachment end 25 to the backing plate 12. The fabric strap 22 is provided with a plurality of fabric loops 23. When the tourniquet cuff 10 is wrapped around a patient's limb so that the flexible covering 14 is in contact with the limb, the fabric strap 22 is also wrapped around the limb to allow locking engagement of the loops 23 of the fabric strap 22 with hooks 21 of the fabric strip, holding the tourniquet cuff 10 in position about the limb. Additional securement of the tourniquet cuff 10 is possible with a tie 26.

After the tourniquet cuff 10 is secured in position about a patient's limb, it can be inflated to apply radially directed inward pressure to the limb. Sufficient pressure is applied to the limb to effectively limit blood flow in the limb distal with respect to the tourniquet cuff 10. In the embodiment illustrated in FIGS. 1-3, an inflatable bladder 30 is disposed within an inflation cavity 28 defined between the backing plate 12 and flexible covering 14. The inflatable bladder 30 is not fixed into position by stitching or other type of attachment, but instead freely floats in the inflation cavity 28. Inflation of the inflatable bladder 30 outwardly forces the flexible covering 14 and, to a lesser degree because of its semirigid structure, the backing plate 12, imposing circulation cutting pressure to the limb.

The inflatable bladder 30 is formed from the combination of a first air impermeable layer 32 and a second air impermeable layer 34, which together define a bladder chamber 36 therebetween. The layers 32 and 34 are joined at their edges by a sealed periphery 38. A conduit 40 (along with its coupling piece 42) is in fluid communication with the bladder chamber 36. The conduit 40 is in sealed attachment to the first air impermeable layer 34, which passes therethrough to allow air admittance or withdrawal from the bladder chamber 36 by way of the conduit 40. The coupling piece 42 can be attached to any conventional air inflation device to allow inflation of the bladder chamber 36, and deflation simply requires fluid connection with the atmosphere.

Preferably, the first and second air impermeable layers 32 and 34 are formed from polymer impregnated or coated fabrics. For example, nylon impregnated with polyurethane may be used to form layers 32 and 34. The periphery 38 of the layers 32, 34 can be sealed by RF, heat, or ultrasonic welding, or can optionally be sealed with adhesives.

Figure 4:
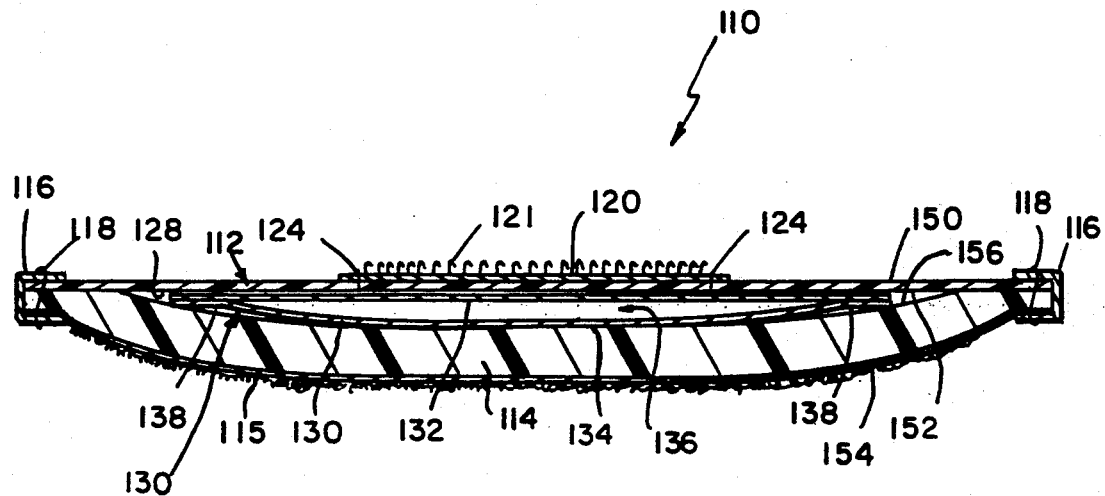
FIG. 4 is a transverse cross sectional view taken across the width of an alternative embodiment of a tourniquet cuff, showing an inflatable bladder and backing plate similar to that illustrated in FIG. 1, but also illustrating a padded flexible covering having a outer surface provided with a plurality of fabric loops.
Figure 5:
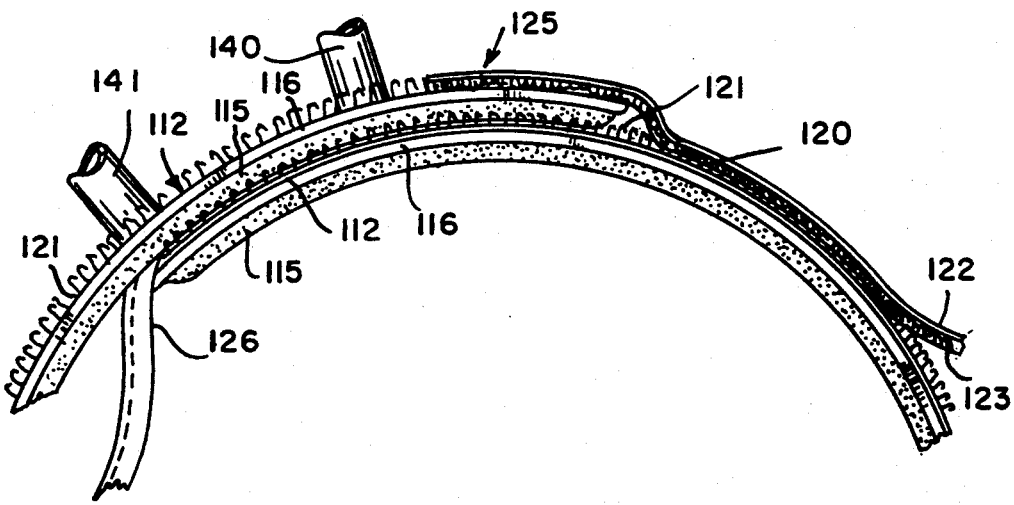
FIG. 5 is a longitudinal cross sectional view taken along the length of the tourniquet cuff illustrated in FIG. 4, showing a tourniquet cuff wrapped around and sejoined to itself in a normal operating position, with the fabric loops engaged with fabric hooks attached to the backing plate, the engagement stabilizing the tourniquet cuff and preventing lateral telescoping movement of one end the tourniquet cuff relative to the other end of the tourniquet cuff.

An alternative embodiment is illustrated in FIGS. 4–5, which shows a disposable tourniquet cuff 110. Unless otherwise indicated, corresponding numbers (eg., 18 corresponds to 118) indicate substantially identical structures for the two illustrated embodiments. Materials, construction, and alternative indicated embodiments similarly correspond.

The tourniquet cuff 110 includes a backing plate 112 having an outer side 150 and an inner side 152. The backing plate 112 is substantially identical in form and construction to the backing plate 12 previously described and illustrated in FIGS. 1-3. A flexible covering 114 having and outer side 154 and an inner side 156 is also provided. The flexible covering 114 is not substantially identical to flexible covering 14 illustrated in FIGS. 1-3, but is instead manufactured from a thick foam pad intended to enhance patient comfort. Open-celled polyurethane foams may be used, as well as other conventional padding foams known to those skilled in the art. The outer side 154 of the flexible covering 114 presents an engagable fabric layer 115 permanently attached to the foam pad, the engagable fabric layer 115 having fabric loops engagable by fabric hooks 121.

The backing plate 112 is attached by stitching 118 to a flexible covering 114, in substantially the same manner as backing plate 12 is attached to flexible covering 14. Both the backing plate 112 and the flexible covering 114 are generally rectangular in shape, and the dimensions of backing plate 112 and flexible covering 114 are matched, with the respective length and width being substantially equivalent. The tourniquet cuff 110 can be provided in varying lengths or widths to accommodate differing limb size.

Like tourniquet cuff 10, the tourniquet cuff 110 is wrapped around and securely attached to itself using a strip 120 permanently mounted on the outer side 150 of the backing plate 112. The strip 120 is provided with a plurality of fabric hooks 121. In addition, a fabric strap 122 is attached at its attachment end 125 to the backing plate 12. The fabric strap 122 is provided with a plurality of fabric loops 123. When the tourniquet cuff 110 is wrapped around a patient's limb so that the flexible covering 114 is in contact with the limb, the fabric strap 122 is also wrapped around the limb to lockingly engage loops 123 of the fabric strap 122 with hooks 121 of the fabric strip. In addition, as best seen in FIG. 5, the fabric hooks 121 lockingly engage the engagable fabric 115. This secondary engagement prevents telescoping of tourniquet cuff 110, securely holding the tourniquet cuff 110 in position about the limb without lateral movement during inflation.

As will be appreciated by those skilled in the art, engagement mechanisms other than fabric hook and loops may be used. Raised fabric surfaces, conventional belts or ties, hooks, catches, snap-fit buttons, adhesives, or other fastening mechanisms for engaging self-attachment of the tourniquet cuff 10 may be employed. Such fasteners or engagement mechanisms may be used alone or in conjunction with other fasteners or engagement mechanisms, depending upon the specific application.

In the embodiment illustrated in FIGS. 4–5, an inflatable bladder 130 is disposed within an inflation cavity 128 defined between the backing plate 112 and flexible covering 114. The inflatable bladder 130 may preferably be fixed into position by adhesive attachment to inner side 152 of the backing plate 112. Like the inflatable bladder 30, inflation of the inflatable bladder 130 outwardly forces the flexible covering 114 to impose circumferential pressure to the limb.

Like inflatable bladder 30, the inflatable bladder 130 is formed from the combination of a first air impermeable layer 132 and a second air impermeable layer 134, which together define a bladder chamber 136 therebetween. The layers 132 and 134 are joined at their edges by a sealed periphery 138. Two conduits, inlet conduit 140 and outlet conduit 141 are fluid communication with the bladder chamber 136. The conduits 140, 141 can be used alternatively to inflate the bladder 130 and release pressurized air.

Although preferred embodiments are disclosed, it will be appreciated that various modifications and changes can be made without departing from the scope and spirit of the invention as defined in the following claims:

I claim:

1. A tourniquet cuff for reducing blood flow in a patient's limb, the tourniquet comprising,
   a backing plate having an inner and outer side,
   a flexible covering having an inner and outer side, formed to be substantially more pliable than the backing plate, the backing plate and the flexible covering being attached together to define an inflation cavity between the inner side of the backing plate and the inner side of the flexible covering,
   an inflatable bladder positioned in the inflation cavity, and
   means for securing the tourniquet about a patient's limb with the outer side of the flexible covering in contact with the patient's limb.

2. The tourniquet of claim 1, further comprising a border strip positioned for stitching attachment of the backing plate and the flexible covering.

3. The tourniquet of claim 2, wherein the flexible covering is attached to the backing plate by stitching extending through the flexible border strip, the backing plate, and the flexible covering.

4. The tourniquet of claim i, wherein the inflatable bladder further comprises first and second air impermeable layers attached together by an air impermeable seal at their peripheries to provide a bladder chamber defined between the first and second air impermeable layers, and means for inflating the bladder chamber.

5. The tourniquet of claim 4, wherein the inflating means includes conduit situated to extend through the backing plate and join in fluid communication with the bladder chamber.

6. The tourniquet of claim 5, wherein the inflating means includes a coupling piece attached to the conduit, the coupling piece being configured for attachment to a pressurized air source.

7. A disposable tourniquet cuff comprising,
   a backing plate formed from a semirigid material and having an inner and outer side,
   a flexible covering having an inner and outer side, formed to be substantially more pliable than the semirigid backing plate, and attached to the backing plate to define an inflation cavity between the inner side of the backing plate and the inner side of the flexible covering, an inflatable bladder positioned in the inflation cavity, the inflatable bladder having first and second air impermeable fabric layers formed by impregnation of fabric with polymeric material, the first and second air impermeable fabric layers attached together by an air impermeable seal at their peripheries to provide a bladder chamber defined therebetween, and means for inflating the bladder chamber, and means for securing the tourniquet about a patient's limb.

8. The tourniquet of claim 7, further comprising a flexible border strip peripherally attached to both the outer side of the backing plate and the outer side of the flexible covering.

9. The tourniquet of claim 8, wherein the flexible covering is attached to the backing plate by stitching extending through the flexible border strip, the backing plate, and the flexible covering.

10. The tourniquet of claim 9, wherein the backing plate and the flexible covering have substantially identical rectangular shapes.

11. A tourniquet cuff for reducing blood flow in a patient's limb, the tourniquet comprising, a backing plate having an inner and outer side, a strip supporting a plurality of fabric hooks, the strip being attached to the outer side of the backing plate, a fabric strap attached at one end to the outer side of the backing plate, the fabric strap supporting a plurality of fabric loops for engagement with the fabric hooks, a flexible covering having an inner and outer side, formed to be substantially more pliable than the backing plate, the backing plate and the flexible covering being attached together to define an inflation cavity between the inner side or the backing plate and the inner side of the flexible covering, and the outer side of the flexible covering presenting an engagable surface for engagement with the fabric hooks to augment securement of the tourniquet about a patient's limb, and an inflatable bladder positioned in the inflation cavity, the bladder being inflatable to reduce blood flow in a patient's limb when the tourniquet cuff is wrapped around a patient's limb, the fabric strap is securely attached to the strip, and the strip engages the engagable surface of the flexible covering.

12. The tourniquet of claim 11, further comprising a border strip positioned for stitching attachment of the backing plate and the flexible covering.

13. The tourniquet of claim 12, wherein the flexible covering is attached to the backing plate by stitching extending through the flexible border strip, the backing plate, and the flexible covering.

14. The tourniquet of claim 11, wherein the inflatable bladder further comprises first and second air impermeable layers attached together by an air impermeable seal at their peripheries to provide a bladder chamber defined between the first and second air impermeable layers, and means for inflating the bladder chamber.

15. The tourniquet of claim 14, wherein the inflating means includes an inlet conduit situated to extend through the backing plate and join in fluid communication with the bladder chamber.

16. The tourniquet of claim 15, wherein the inflating means includes an outlet conduit situated to extend through the backing plate into the bladder chamber and allows release of pressurized air.

17. A tourniquet cuff for reducing blood flow in a patient's limb, the tourniquet comprising, a backing plate having an inner and outer side, a flexible covering having an inner and outer side, the flexible covering being formed to be substantially more pliable than the backing plate, and the backing plate and the flexible covering being attached together to define an inflation cavity between the inner side of the backing plate and the inner side of the flexible covering, an inflatable bladder positioned in the inflation cavity, means for wrappably attaching the tourniquet cuff to itself, and means for engaging the outer side of the flexible covering to augment securement of the tourniquet cuff about a patient's limb and minimize telescoping lateral movement of the tourniquet.

18. The tourniquet of claim 17, wherein the flexible covering is padded to distribute application of circumferential pressure to a patient's limb and enhance patient comfort.

19. The tourniquet of claim 18, wherein the flexible covering is substantially formed from a polymeric foam attached to the backing plate by stitching extending through both the backing plate and the flexible covering.

20. The tourniquet of claim 17, wherein the inflatable bladder further comprises first and second air impermeable layers attached together by an air impermeable seal at their peripheries to provide a bladder chamber defined between the first and second air impermeable layers, and means for inflating the bladder chamber.

21. The tourniquet of claim 20, wherein the inflating means includes at least one conduit situated to extend through the backing plate and join in fluid communication with the bladder chamber.

* * * * *